United States Patent [19]
Jamison, Jr. et al.

[11] Patent Number: 5,199,418
[45] Date of Patent: Apr. 6, 1993

[54] MOUTH SPECULUM

[76] Inventors: Robert G. Jamison, Jr., P.O. Box 57, Evans City, Pa. 16033; Louis D. Jeffrey, 14805 Branched Oak Rd., Waverly, Nebr. 68462

[21] Appl. No.: 881,057
[22] Filed: May 11, 1992
[51] Int. Cl.$^5$ .......................... A61B 1/06; A61D 1/08
[52] U.S. Cl. ........................ 128/13; 128/14; 362/205
[58] Field of Search ................. 128/3, 12-19, 128/20; 119/129; 362/202-204, 195, 205, 208

[56] References Cited

U.S. PATENT DOCUMENTS

| | | | |
|---|---|---|---|
| 455,972 | 7/1891 | Oudin et al. | 128/16 |
| 1,249,574 | 12/1917 | Werner | 362/205 |
| 1,986,010 | 1/1935 | O'Laughlin | 285/115 |
| 3,568,664 | 3/1971 | Meriwether | 128/14 |
| 4,380,888 | 4/1983 | Lanham | 54/8 |
| 4,802,851 | 2/1989 | Rhoades | 433/93 |

FOREIGN PATENT DOCUMENTS

| | | | |
|---|---|---|---|
| 4759 | of 1906 | United Kingdom | 128/14 |
| 210600 | 2/1924 | United Kingdom | 128/13 |

Primary Examiner—Richard J. Apley
Assistant Examiner—Donna Maraglio
Attorney, Agent, or Firm—Zarley, McKee, Thomte, Voorhees & Sease

[57] ABSTRACT

A mouth speculum includes a first elongated hollow tubular member connected generally perpendicularly to a second elongated hollow tubular member to form a general T-shaped member. The second hollow tubular member has an opening formed in a rearward end to receive a person's thumb to support the mouth speculum thereon. In the preferred embodiment of the invention the first elongated member has a window formed therein with a light bulb mounted behind the window to provide illumination.

7 Claims, 1 Drawing Sheet

MOUTH SPECULUM

TECHNICAL FIELD

The present invention relates generally to apparatus for examining the oral cavity of horses and other animals, and more particularly to an improved mouth speculum which will hold the mouth of the animal open for inspection.

BACKGROUND OF THE INVENTION

It is frequently necessary for a veterinarian to examine the mouth of an animal. Such a practice can be difficult and frustrating, since most animals do not particularly enjoy such examinations.

Similarly, the owner or trainer of a horse or other animal is often required to maintain the animal's mouth open for inspection or the administration of medicine. Such a task is even more difficult for the untrained pet owner.

It is therefore an object of the present invention to provide an improved mouth speculum which is quick and simple to utilize by even an untrained person.

Another object of the present invention is to provide a mouth speculum which may be used in one hand, thereby permitting free use of the second hand.

Yet another object is to provide a mouth speculum which is simple and economical to manufacture.

These and other objects will be apparent to those skilled in the art.

SUMMARY OF THE INVENTION

The mouth speculum of the present invention includes a first elongated hollow tubular member connected generally perpendicularly to a second elongated hollow tubular member to form a general T-shaped member. The second hollow tubular member has an opening formed in a rearward end to receive a person's thumb to support the mouth speculum thereon. In the preferred embodiment of the invention the first elongated member has a window formed therein with a light bulb mounted behind the window to provide illumination. Batteries and a switch are mounted within the speculum to selectively power the light bulb. Caps are provided on the ends of the first tubular member to seal the light bulb within the mouth speculum.

DESCRIPTION OF THE PREFERRED EMBODIMENT

Figure 1:
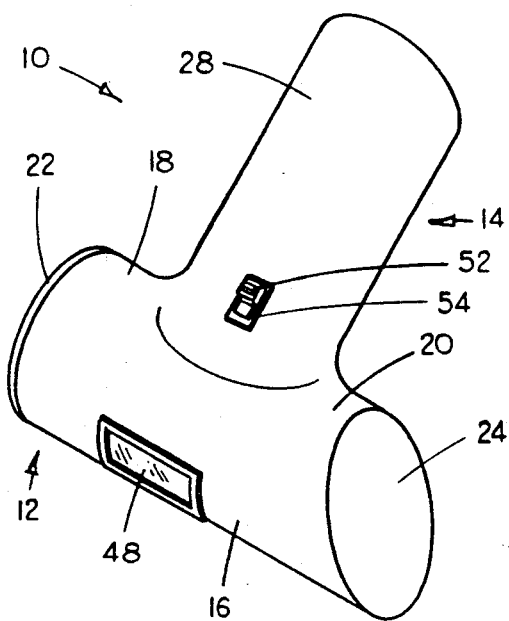
FIG. 1 is a perspective view of the speculum of the present invention.

Referring now to the drawings, in which similar or corresponding parts are identified with the same reference numeral, and more particularly to FIG. 1, the mouth speculum of the present invention is designated generally at 10 and includes a spreader portion 12 and a support portion 14.

Spreader portion 12 is formed from a hollow cylindrical tube 16 having first and second ends 18 and 20 respectively. A cap 22 is removably mounted on end 18, and a cap 24 is formed on end 20 so as to completely seal the interior cavity 26 (see FIG. 2) of tube 16.

Figure 2:
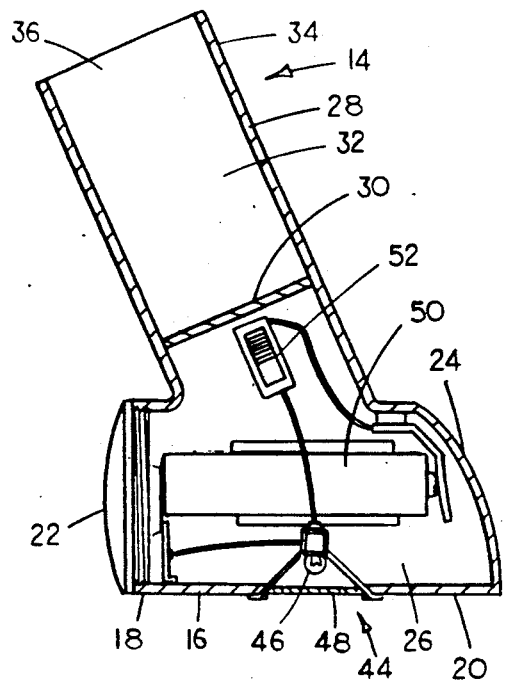
FIG. 2 is a cross-sectional view taken at lines 2—2 in FIG. 1.

Support portion 14 is formed from a second hollow cylindrical tube 28 which is connected generally perpendicularly to first tube 16 to form a generally T-shaped speculum 10. The interior of tube 28 preferably communicates with cavity 26 as shown in FIG. 2. A wall 30 may be installed in the interior of second tube 28 to separate the generally T-shaped cavity 26 from the rearward elongated cylindrical cavity 32 extending from wall 30 to the rearward end 34 of second tube 28. Preferably, rearward end 34 of second tube 28 has an opening 36 to permit the insertion of a person's thumb within cylindrical cavity 32. In this manner, mouth speculum 10 may be supported in one hand on the user's thumb.

Figure 3:
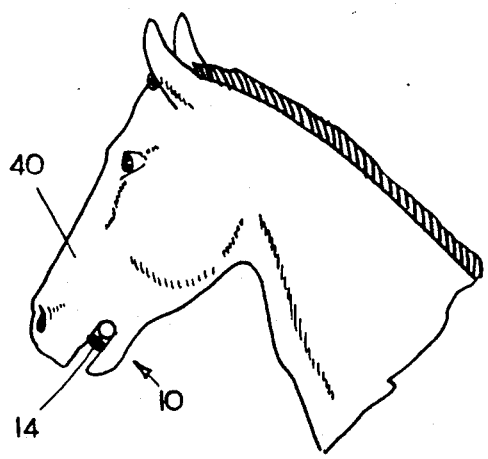
FIG. 3 is a side view of the invention with the device inserted in an animal's mouth.
Figure 4:
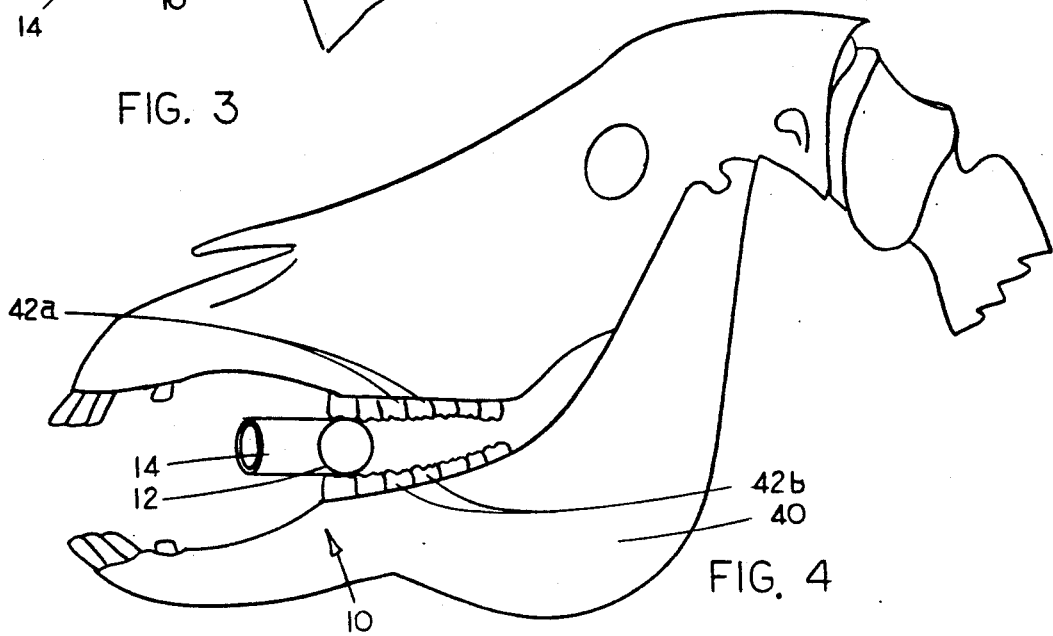
FIG. 4 is an enlarged side view showing the invention relative to a horse's bone structure.

Referring now to FIGS. 3 and 4, mouth speculum 10 is used by placing the user's thumb in the rearward end of support portion 14 to support speculum 10. Although FIGS. 3 and 4 show a horse's mouth 40, the speculum 10 could be used for other animals. Once the horse's mouth 40 is opened, spreader portion 12 is inserted between the upper and lower molars 42a and 42b respectively to maintain the open position of mouth 40. An examination of the oral cavity may then be conducted, leaving the user's other hand free to handle other instruments or medications.

It is frequently desirable to illuminate the interior of the oral cavity for examination. For this reason, a light 44 may be provided within speculum 10. As shown in FIG. 2, light 44 includes a light bulb 46 mounted in first tube 16 directly aligned with a clear window 48 formed in the forward surface of first tube 16. A battery 50 is mounted within tube 16 and has one pole electrically connected to light bulb 46 and the other pole electrically connected to a switch 52. As shown in FIG. 1, switch 52 preferably extends through an aperture 54 in second tube 28 to permit activation of light bulb 46 from the exterior of mouth speculum 10.

Whereas the invention has been shown and described in connection with the preferred embodiment thereof, it will be understood that many modifications, substitutions and additions may be made which are within the intended broad scope of the appended claims. There has therefore been shown and described an improved mouth speculum which at least accomplishes at least all of the above stated objects.

We claim:
1. An illuminated mouth speculum, comprising:
   a first tubular elongated member having first and second ends, a hollow interior cavity, a forward portion, and a rearward portion;
   a second elongated member affixed at a forward end to the rearward portion of said first tubular member intermediate said first and second end and extending generally perpendicularly therefrom;
   said second member having a rearward end with an opening therein communicating with an interior cavity extending longitudinally and forwardly within said second member from the rearward end thereof, said cavity formed of a length sufficient to receive at least a portion of a person's thumb to support said mouth speculum thereon;
   a first cap removably mounted on the first end of said first member to enclose the cavity in said first member;

window means formed in the forward portion of said first member permitting the passage of light from said first member cavity; and a light source selectively operably mounted within a portion of said first member.

2. The mouth speculum of claim 1, wherein said first and second members are formed of a water resistant material.

3. The mouth speculum of claim 1, wherein said cavity in said second member extends forwardly to communicate with the cavity of said first member.

4. The mouth speculum of claim 3, further comprising a second cap mounted on the second end of said first member to enclose the cavity in said first member.

5. The mouth speculum of claim 4, wherein said light source includes:

a light bulb mounted in said first tube at a location to provide illumination through said window means;

power means mounted in said speculum and electrically connected to said light bulb to power said light bulb; and switch means electrically connected between said light bulb and power means to selectively open and close the electrical connection between the power means and light bulb.

6. The mouth speculum of claim 4, wherein said window means includes an opening formed in the forward portion of said first member and transparent material mounted in said opening.

7. The mouth speculum of claim 4, wherein said window means is a transparent portion formed in the forward portion of said first member.

* * * * *